United States Patent [19]
Mitzlaff

[11] 4,138,408
[45] Feb. 6, 1979

[54] ω-ALKOXY DERIVATIVES OF LACTAMS AND PROCESS FOR THEIR MANUFACTURE

[75] Inventor: Michael Mitzlaff, Bad Homburg, Fed. Rep. of Germany

[73] Assignee: Hoechst Aktiengesellschaft, Frankfurt am Main, Fed. Rep. of Germany

[21] Appl. No.: 825,379

[22] Filed: Aug. 17, 1977

Related U.S. Application Data

[62] Division of Ser. No. 751,335, Dec. 16, 1976, abandoned.

[30] Foreign Application Priority Data

Dec. 20, 1975 [DE] Fed. Rep. of Germany ....... 2557765

[51] Int. Cl.² .......................................... C07D 207/26
[52] U.S. Cl. ............................ 260/326.45; 260/239 B; 260/326.5 FL; 424/274; 542/426; 542/427; 546/220; 546/243
[58] Field of Search ................... 260/326.45; 542/426, 542/427

[56] References Cited

U.S. PATENT DOCUMENTS 4,096,274   6/1978   Reuschling et al. ................. 424/274

FOREIGN PATENT DOCUMENTS 2452536   5/1976   Fed. Rep. of Germany ...... 260/326.45

*Primary Examiner*—Jose Tovar
*Assistant Examiner*—Mary Lee
*Attorney, Agent, or Firm*—Curtis, Morris & Safford

[57] ABSTRACT

Compounds of the formula

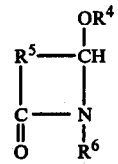

in which $R^4$ represents an alkyl radical having from 1 to 4 carbon atoms, $R^5$ represents a linear or branched alkylene radical having from 1 to 10 carbon atoms in the chain which may be substituted by groups which are not reactive under the applied conditions, and $R^6$ represents hydrogen or a branched alkyl radical having from 3 to 10 carbon atoms with a secondary or tertiary N-α-C atom, are prepared by anodic alkoxylation of lactams of the formula

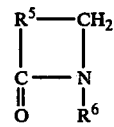

with an alcohol of the formula $R^4OH$, in which formulae $R^4$, $R^5$ and $R^6$ have the aforesaid meaning, in the presence of at least one alkali metal or tetraalkylammonium tetrafluoroborate, hexafluoroborate or nitrate as conducting salt, at a temperature of up to about 100° C. in an electrolytic cell with stationary or flowing electrolyte. Some of the products are novel. They can be used as intermediates for the manufacture of pharmaceuticals, antistatic agents in textile industries and as intermediates for polymerization reactions and for the preparation of α-amino-α,ω-dicarboxylic acids.

4 Claims, 1 Drawing Figure

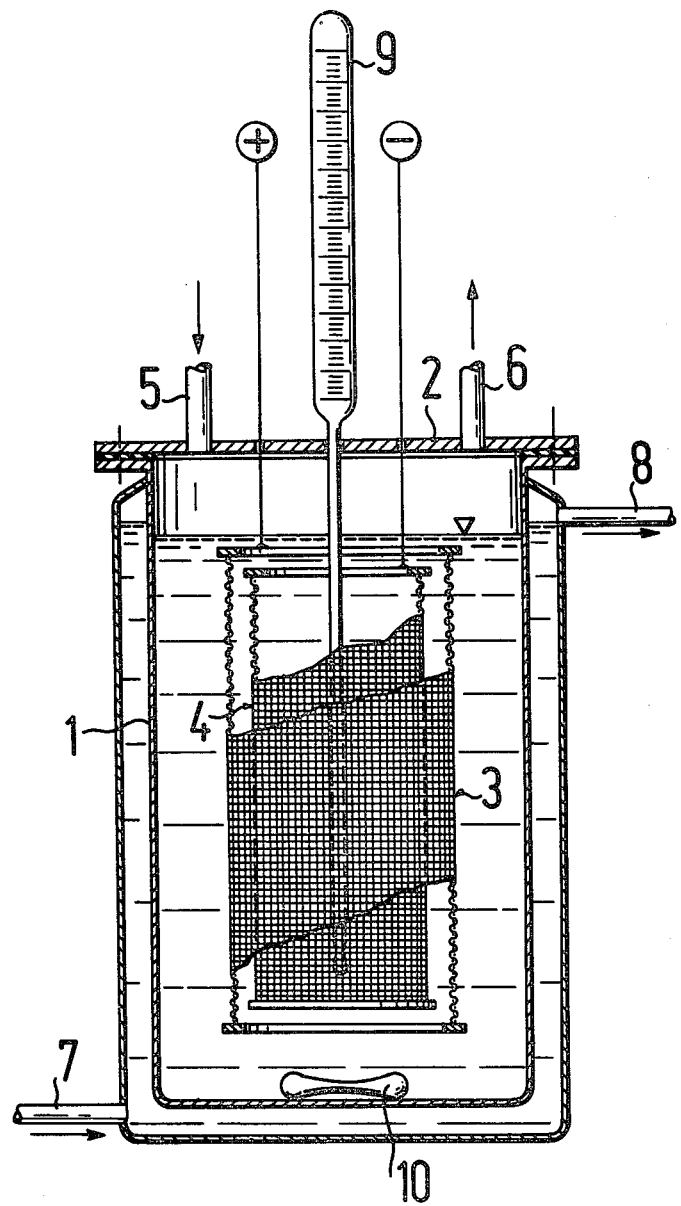

ω-ALKOXY DERIVATIVES OF LACTAMS AND PROCESS FOR THEIR MANUFACTURE

This is a division, of application Ser. No. 751,335 filed Dec. 16, 1976 now abandoned.

This invention relates to ω-alkoxy derivatives of lactams and to a process for their manufacture.

It has been proposed to react, by an electrochemical process, carboxylic acid amides alkylated on the nitrogen atom of the formula

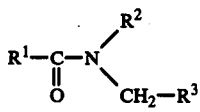

in which $R^1$, $R^2$ and $R^3$ represent hydrogen or organic radicals and $R^1$ and $R^2$ may also be linked with each other, with alcohols to obtain the corresponding N-α-alkoxyalkyl carboxylic acid amides (German Offenlegungsschrift 2,113,338). In this process the N-alkylcarboxylic acid amides are electrolyzed in an excess of an alcohol in the presence of a conducting salt, for example an alkali metal or a tetraalkyl ammonium tetrafluoroborate, hexafluorophosphate or nitrate, at a temperature of up to about 100° C. The electrolytic cell may contain a stationary or a flowing electrolyte and the amount of current used does not exceed 2.4 Faradays per mol of carboxylic acid amide.

It has also been proposed (Belgian Pat. No. 837,906) to electrolyze starting products specifically mentioned in the DOS 2,113,338, i.e. N-alkylcarboxylic acid amides of the formula

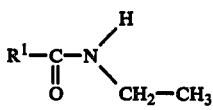

in which $R^1$ has the aforesaid meaning, in the presence of very specific conducting salts to obtain the corresponding N-α-alkoxyalkyl carboxylic acid amides. In this process higher amounts of current can be used and, hence, the substance yield is improved and, moreover, the reaction mixture can be worked up more easily.

In the aforesaid processes the starting materials used are exclusively N-alkylcarboxylic acids which carry 2 hydrogen atoms in at least one N-alkyl group in α-position to the nitrogen and carry also the group $CH_2$-$R^3$ on the nitrogen, especially when $R^1$ and $R^2$ are linked with each other.

Still further, it has been proposed to alkoxylize at the anode substantially in the same manner those N-alkylcarboxylic acid amides which carry on the nitrogen atom two alkyl groups linked with each other (cf. German Offenlegungsschrift 2,539,777). In the latter process the starting compounds have the formula

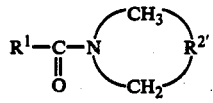

in which $R^1$ has the aforesaid meaning and $R^{2'}$ represents a linear or branched alkylene radical having from 1 to 4 carbon atoms in the chain. Depending on the current amount used, the alkoxylation is effected on one or on both of the $CH_2$ groups linked to the nitrogen atom.

In the anodic alkoxylation of the N-alkylcarboxylic acid amides used according to the process of DOS 2,113,338 it is practically always the $CH_2$ group of the $CH_2$-$R^3$ substituent which is alkoxylated even if the radicals $R^1$ and $R^2$ are linked with each other, i.e. lactams substituted at the nitrogen atom by the group $CH_2$-$R^3$. Products alkoxylated on the nucleus, that is to say in the lactam ring, are practically not formed.

There are known purely chemical reactions to prepare lactams which additionally carry an alkoxy group on the carbon atom adjacent to the nitrogen atom (opposite to the carbonyl group). Compounds of this type can also be considered N,O-acetals. A chemical method to prepare these compounds is described, for example, in Liebigs Ann. Chem. 1974, pages 539–560, according to which the four-membered ring compounds are prepared, in principle, by the following reaction equation:

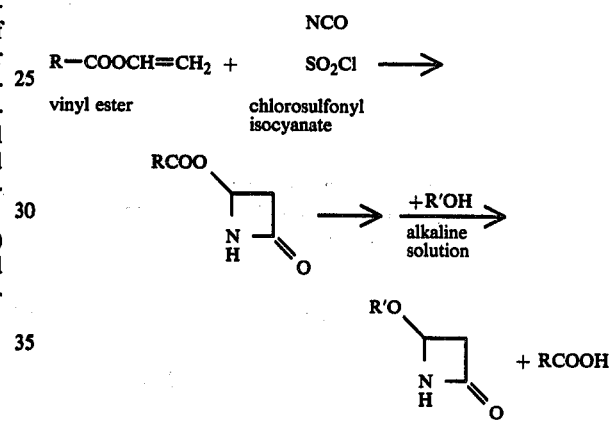

in which R and R' represent organic radicals.

A generalization of this method for the preparation of N,O-acetals with higher rings has not yet become known.

In view of the fact that N,O-acetals of this type are important intermediates it is desirable to develop a process permitting the preparation of such compounds in a simple and uncomplicated manner independent of the size of the lactam ring.

This problem could be solved by further developing the alkoxylation reaction described in German Offenlegungsschrift No. 2,113,338 and in Belgian Pat. No. 837,906.

It is therefore the object of the present invention to use as starting materials for the electrolysis lactams of the formula

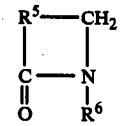

in which $R^5$ represents a linear or branched alkylene radical having from 1 to 10 carbon atoms in the chain which may be substituted by groups which are not reactive under the applied conditions, for example hydroxyl or halogen, preferred substituents of $R^5$ being CH$_2$OH—, —CH$_2$—A—CH$_2$CH$_2$CH$_2$—COOR$^7$ in which A represents —C≡C—, —CH=CH— or —CH$_2$—CH$_2$— and R$^7$ stands for hydrogen or a low molecular weight aliphatic (C$_1$–C$_4$), cycloaliphatic (C$_5$–C$_6$) or araliphatic (C$_6$–C$_8$) hydrocarbon radical, R$^6$ represents hydrogen or a branched alkyl radical preferably having from 3 to 10 carbon atoms with a secondary or tertiary N-α-C atom which is difficult to alkoxylate.

The present invention provides a process for the anodic alkoxylation of N-alkylcarboxylic acid amides with an alcohol of the formula R$^4$OH in which R$^4$ represents an alkyl radical having from 1 to 4 carbon atoms, in the presence of at least one alkali metal or tetraalkylammonium tetrafluoroborate, hexafluorophosphate or nitrate as conducting salt, at a temperature of up to about 100° C. in an electrolytic cell with stationary or flowing electrolyte, which comprises using as N-alkyl carboxylic acid amide a lactam of the formula

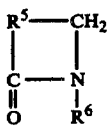

in which R$^5$ and R$^6$ have the aforesaid meaning. The reaction yields lactams alkoxylated in the nucleus and having the following formula Suitable starting compounds in the process of the invention are, for example, azetidinone-2, 3-methyl-azetidinone-2, 1-isopropylpyrrolidone-2, 1-isopropyl-4-hydroxymethyl-pyrrolidone-2, 1-isopropyl-3-[6-carbomethoxy-2-hexine-yl(1)]-4-hydroxymethylpyrrolidone-2, 1-tert.-butylpyrrolidone-2, piperidone-2, ε-caprolactam, the lactams of ω-amino-caprylic acid, capric acid, lauric acid, preferably, however, 1-isopropyl-4-hydroxymethylpyrrolidone-2, compounds of the formula

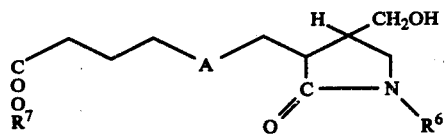

in which R$^7$ represents a C$_1$–C$_4$ alkyl radical, a C$_5$–C$_6$ cycloalkyl radical or an araliphatic radical, and more preferably 1-isopropyl-3-[6-carbomethoxy-2-hexine-yl(1)]-4-hydroxymethyl-pyrrolidone-2, (in which A is —C≡C—, R$^6$ is

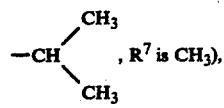

, R$^7$ is CH$_3$), which compounds can be prepared as described in German Offenlegungsschriften Nos. 2,452,536 and 2,528,036 according to the following reaction scheme:

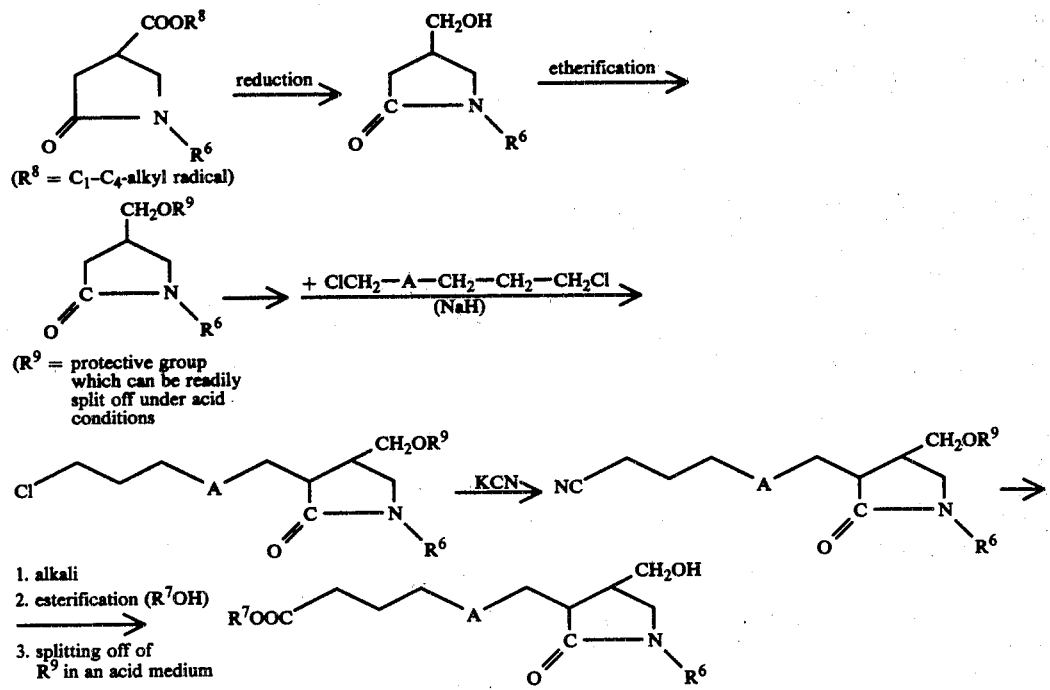

1. alkali
2. esterification (R$^7$OH)
3. splitting off of R$^9$ in an acid medium

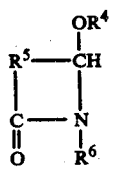

In the case of A being —C≡C— the final compound can be partially hydrogenated to form the —CH=CH— group or completely hydrogenated to —CH$_2$—CH$_2$— by a method known per se.

With the use of the preferred starting compounds the following final compounds are obtained:

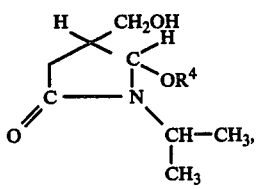

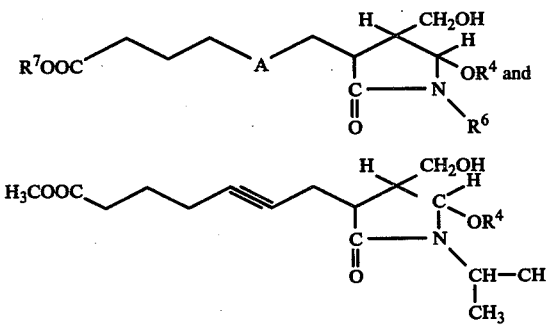

Products of this type are novel. The latter two compounds can be used as intermediates for the manufacture of pharmaceuticals, especially those having prostaglandine-like effects (cf. Application Ser. No. 751,165, filed Dec. 16, 1976, now U.S. Pat. No. 4,096,274 filed concurrently herewith).

A pharmaceutical of this type is, for example, the compound of the formula

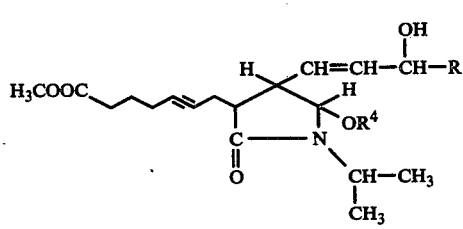

obtained by oxidation of the $CH_2OH$ group in the latter compound to the CHO group, reaction with

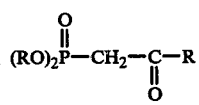

in which each R stands for an alkyl radical and the radical R bound to the

may also represent an optionally substituted phenoxy or cycloalkyl radical, and hydrogenation of the azetocarbonyl group.

Further preferred starting compounds in the process of the invention are lactams with 5 to 13 ring members of the formula

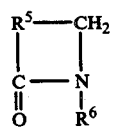

in which
$R^5$ represents $-(CH_2)_{2-10}$, preferably $-(CH_2)_3-$, $-(CH_2)_4-$ and $-(CH_2)_{10}-$,
$R^6$ stands for hydrogen or a branched alkyl radical having from 3 to 10 carbon atoms with a secondary or tertiary N-α-C atom, preferably hydrogen.

The compounds obtained in this manner are also novel, they have the formula

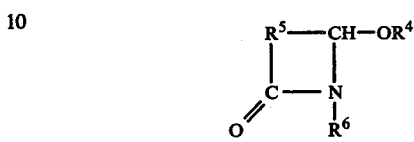

in which
$R^5$ and $R^6$ have the aforesaid meaning, $R^4$ represents an alkyl radical with 1 to 4 carbon atoms preferably $CH_3$. Compounds of this type can be used as antistatic agents in textile industries and as intermediates in polymerization reactions and in the preparation of α-amino-α, ω-dicarboxylic acids according to the following reaction scheme:

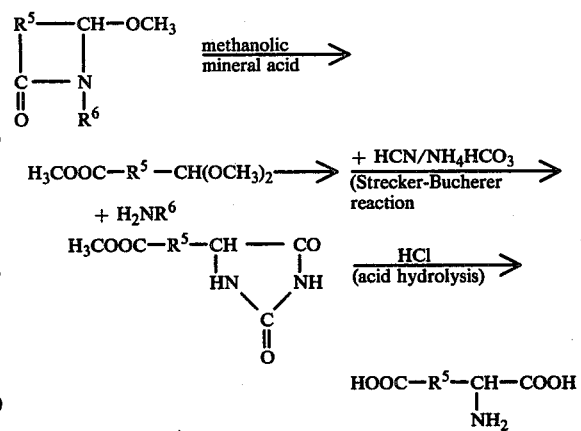

Suitable alcohols $R^4OH$ to carry out the process of the invention are methanol, ethanol, n-propanol, isopropanol, n-butanol, sec.-butanol, preferably, however, methanol and ethanol and more preferably methanol.

The conducting salt to be used in the process of the invention are alkali metal salts (Li, Na, K, Rb, Cs) and tetraalkyl ammonium salts of tetrafluoroboric acid, hexafluorophosphoric acid and nitric acid. They are used either singly or in admixture with one another. The alkyl radicals in the tetraalkyl ammonium group have 1 to 6 and preferably 1 to 4 carbon atoms, especially the methyl and ethyl radical. The following conducting salts are mentioned by way of example: Na-tetrafluoroborate, Na-nitrate, K-tetrafluoroborate, K-hexafluorophosphate, Rb-nitrate, tetramethylammonium tetrafluoroborate, tetraethylammonium tetrafluoroborate, tetra-n-butylammonium tetrafluoroborate, tetraethylammonium hexafluorophosphate, tetra-n-propylammonium hexafluorophosphate, tetra-n-butylammonium hexafluorophosphate, or tetramethylammonium nitrate. Preferred conducting salts are the alkali metal and tetraalkyl ammonium tetrafluoroborates especially $NaBF_4$, $KBF_4$ and $(CH_3)_4-NBF_4$.

The concentration of conducting salt in the electrolysis solution should be in the range of from about 0.01 to about 2.0 mol/l, preferably about 0.02 to 1.0 mol/l. The temperature of the electrolysis solution should be in the range of from about −10° to +100° C., preferably about 0° to 60° C.

In the electrolytic solution the molar proportion of starting acid amide to alcohol is in the range of from about 1:1 to about 1:100, preferably 1:2 to 1:60 and more preferably 1:5 to 1:50.

The electrochemical alkoxylation according to the invention may be carried out discontinuously or continuously.

The process will now be described in further detail by way of example only, with reference to the accompanying drawing which is a view, partly in section, of an electrolysis cell suitable for carrying out the process of the invention in discontinuous manner.

Referring to the drawing, an electrolytic cell (1) is equipped with a tightly sealing cover or lid (2), through which the power supply lines for electrodes (3) and (4) are led and in which an opening (5) for the supply of the electrolysis solution, an opening (6) for the discharge of gas and a thermometer (9) are fitted. The orifice (6) for the discharge of gas may be equipped with a reflux condenser, in which evaporating portions of the electrolysis mixture may be recovered by condensation. The electrolytic cell (1) is encased and may be connected to a heating or cooling liquid circuit by means of inlet and outlet sockets (7 and 8). The temperature of the electrolysis solution is controlled by the thermometer (9) or a thermosensor. The two electrodes (3) (anode) and (4) (cathode) are set up at a distance of from 0.5 to 50 mm, preferably from 1 to 15 mm.

As electrodes there are used nets or sheets of palladium or platinum or noble metal-coated metal electrodes, preferably titanium electrodes, mixed oxide-coated metal electrodes (as anodes), preferably titanium anodes, or graphite plates provided with slits or not. The use of electrode nets is especially advantageous, because these facilitate the discharge of the gaseous hydrogen formed during the electrolysis, and the uniform and thorough mixture of the electrolysis solution is additionally favoured by the gas current formed. The vertical disposition of the electrodes may be replaced, if desired, by a horizontal one. It is also possible to use several electrode pairs; a block-like combination of angular or non-angular capillary split electrodes, optional with vibration of the electrodes, has proved especially efficient. The solution is mixed vigorously during electrolysis by means of an agitator, for example a magnetic stirrer (10) or by circulation by pumping, especially in case of the block-like combinations.

If the process is carried out continuously, an additional orifice may be set in the cover (2) of the electrolysis vessel (1) for pump-circulating the electrolysis solution continuously. A portion of the electrolysis solution which is circulated by pumping is separated for work up of the product. After determination of the ratio of the desired reaction product to the starting material in the electrolysis solution by the nuclear magnetic resonance spectrum or by gas chromatography, the solution is worked up in known manner. The starting materials, recovered upon distillation, may be adjusted to the molar ratio employed and then metered into the continuously recirculating electrolysis solution together with the required quantity of the conducting salt or salts.

The electrolysis may be carried out under normal pressure, but may be performed under reduced pressure. So as to avoid the formation of explosive gas mixtures of hydrogen and air, the addition of an inert gas, e.g. nitrogen, is advantageous.

The conducting salt is suitably added after having prepared the alcoholic solution. However, this order may be changed.

There is no need to exclude water strictly from the electrolyte since minor amounts thereof do not affect the course of reaction.

The process gives an especially high yield and is especially efficient with respect to energy consumed, if the conversion of cyclic carboxylic acid amide is increased, e.g. to more than 99%, this step being also advantageous for a better work up of the electrolysis solution. Therefore, the electrolysis is advantageously continued until practically the total starting material is converted so that there is no need later to separate this from the the reaction product.

The electrolysis current is switched off after having led through the quantity of electricity desired, and the electrolysis discharge is then freed from the conducting salt and worked up in known manner, preferably by distillation. The degree of purity of the product may be determined by a nuclear magnetic resonance spectrum.

The current density is chosen in the range of from about 1 to 50 A/dm$^2$, preferably 2 to 30 A/dm$^2$. Lower current densities are also possible, though they diminish the rate at which the product is formed. The quantity of electricity should be about 2 to 4, preferably 2 to 3.5 and especially 2 to 3 Faradays/mol of starting lactam.

The α-alkoxy derivatives of cyclic carboxylic acid amides prepared according to the electrochemical process of the invention are valuable intermediate products, especially for the manufacture of pharmaceuticals, having, in the first place, prostaglandine like effects and also luteolytic, bronchospasmolytic and/or antihypertensive properties and properties to inhibit the secretion of gastric juice.

The following examples illustrate the invention.

EXAMPLE 1

17.6 g of azetidinone-2- and 39.6 g of methanol are electrolyzed in an electrolytic cell having a capacity of approximately 60 ml in the presence of 0.82 g of tetra-m-propylammonium hexafluorophosphate as conducting salt. As electrodes two concentrically placed platinum net cylinders having 225 meshes per cm$^2$ and diameters of 15 and 30 mm, respectively, and a height of 50 mm are immersed in the solution, the outer electrode being connected as anode. During electrolysis the temperature is maintained at about 10° C. After having switched on the electrolysis direct current, the current density at the anode is 1 A/dm$^2$. The current is switched off after passage of 2.5 Faradays per mol of azetidinone-2. The calculated average cell tension is 29.6 volts. After working up by molecular distillation there are obtained 12.7 g of 4-methoxy-azetidinone-2 (boiling point 41° C. under 0.013 millibar, melting point 62°–63° C.), corresponding to a material yield of 50.9% and a current efficiency of 40.7%.

EXAMPLE 2

In an electrolytic cell as described in Example 1 21.0 g of pyrrolidone-2 and 39.6 g of methanol are electrolyzed in the presence of 0.40 g of tetramethylammonium tetrafluoroborate as conducting salt. After having switched on the electrolysis direct current, the density at the anode is 3 A/dm$^2$. The current is switched off after the passage of 2.0 Faradays per mol of pyrrolidone-2. The calculated average cell tension is 35.2 volts. After working up by molecular distillation, 14.3 g of 5-methoxypyrrolidone-2 are obtained (boiling point 87°–90° C. under 0.14 millibar, melting point 56°–58° C.), corresponding to a material yield and a current efficiency of 50.1% each.

EXAMPLE 3

In an electrolytic cell as described in Example 1 14.7 g of pyrrolidone-2 and 39.5 g of ethanol are electrolyzed in the presence of 0.28 g of tetramethyl ammonium tetrafluoroborate as conducting salt. After having switched on the electrolysis direct current, the anode current density is 3 A/dm$^2$. After having passed 2.0 Faradays per mol of pyrrolidone-2 the current is switched off. The calculated average cell tension is 48.2 volts.

Working up by molecular distillation yields 12.0 g of 5-ethoxypyrrolidone-2 (melting point 54°–56° C.), corresponding to a material yield and a current efficiency of 54.2% each.

EXAMPLE 4

In an electrolytic cell as described in Example 1 10.0 of 1-isopropyl-4-hydroxymethylpyrrolidone and 54.6 g of methanol are electrolyzed in the presence of 0.34 g of tetramethylammonium tetrafluoroborate as conducting salt. After having switched on the electrolysis direct current, the anode current density is 2 A/dm$^2$. After the passage of 2.2 Faradays per mol of 1-isopropyl-4-hydroxymethylpyrrolidone, the current is switched off. The calculated average cell tension is 48.5 volts.

After separation of the methanol and separation by column chromatography (silica gel/chloroform + ethanol [9:1])

9.0 g of 1-isopropyl-4-hydroxymethyl-5-methoxypyrrolidone-2 are obtained, corresponding to a material yield of 75.6% and a current efficiency of 68.7%. NMR characteristics of the compound: NMR 100 millicyles per second; solvent:

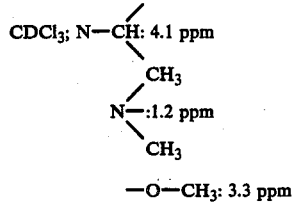

—O—CH$_3$: 3.3 ppm

EXAMPLE 5

(a) Preparation of 1-methyl- and 1-isopropyl-3-[6-carbomethoxy-2-hexine-yl(1)]-4-hydroxymethyl-pyrrolidone 1-methyl compound (α) 29.4 g (138 mols) of 1-methyl-4-(2-tetrahydropyranylhydroxymethyl)-pyrrolidone dissolved in 90 ml of diethyl ether are added over a period of 20 minutes while stirring at −70° C. to 150 mols of LiN(i-C$_3$H$_7$)$_2$ in 150 ml of diethyl ether. Stirring is continued for 45 minutes whereupon the solution is transferred to a coolable dropping funnel (−35° to −40° C.) and added, while stirring over a period of 60 minutes, to a solution cooled to −70° C. of 29.1 g (149 mols) of 1-bromo-6-chloro-hexine(2) in 135 ml of ether. Stirring is continued for another 90 minutes, the mixture is slowly heated to room temperature, 75 ml of water are added dropwise, the organic phase is separated and the aqueous phase is extracted three times, each time with 50 ml of diethyl ether. The combined ether phases are washed three times with 40 ml each of cold sulfuric acid and once with 50 ml of water. After drying and concentrating under reduced pressure the organic phase, 46.6 g of crude 1-methyl-3-[6-chloro-2-hexine-yl(1)]-4-(2-tetrahydropyranyl-hydroxymethyl) pyrrolidone (R$_F$ 0.42 (ethyl acetate)) are obtained The compound is used for the following reaction stage without further purification.

(β) 7.5 g (153 mols) of sodium cyanide are dissolved in 90 ml of dimethyl sulfoxide and the solution is heated to 80° C. 46.6 g (142.5 mmols) of crude 1-methyl-3-[6-chloro-2-hexine-yl(1)]-4-(2-tetrahydropyranyl-hydroxymethyl)-pyrrolidone dissolved in 40 ml dimethyl sulfoxide are then added dropwise while stirring and the mixture is stirred for 3 to 6 hours at 80° C. The course of the reaction is followed by thin layer chromatography (ethyl acetate). When the reaction is terminated, the mixture is cooled to 10° C., 200 ml of water are added and the mixture is extracted three times, each time with 200 ml of diethyl ether. The combined ether phases are washed three times with saturated sodium chloride solution and dried. After concentration under reduced pressure 43.7 g of crude 1-methyl-3-[6-cyano-2-hexine-yl(1)]-4-(2-tetrahydropyranyl-hydroxymethyl)-pyrrolidone [R$_F$ 0.39 (ethyl acetate)] are obtained, which is used for the next reaction without further purification.

(γ) 11 g (0.275 mol) of sodium hydroxide are dissolved in 33 ml of water, 43.7 g (137.5 mols) of 1-methyl-3-[6-cyano-2-hexine-yl(1)]-4-(2-tetrahydropyranyl-hydroxymethyl)-pyrrolidone dissolved in 135 ml of ethyl alcohol are added and the whole is refluxed for 18 hours. The alcohol is removed under reduced pressure, 150 ml of icecold 2N sulfuric acid are added to the residue while cooling with ice and the whole is extracted ten times, each time with 100 ml of diethyl ether. After drying and concentrating the combined ether phases, 47.4 g of crude 1-methyl-3-[6-carbohydroxy-2-hexine-yl)]-4-(2-tetrahydropyranyl-hydroxymethyl)-pyrrolidone are obtained which is directly taken up in 250 ml of methylene chloride and to which 380 ml of a 0.5 molar ethereal diazomethane solution are added at 0° C. The mixture is allowed to stand for 30 minutes at 0° C. and for 1 hour at room temperature. After concentration under reduced pressure, 43.7 g of crude 1-methyl-3-[6-carbomethoxy-2-hexine-yl(1)]-4-(2-tetrahydropyranyl-hydroxymethyl)-pyrrolidone [R$_F$ 0.45 (ethyl acetate)] are obtained.

(δ) The product obtained is dissolved in 200 ml of methanol, 3 drops of concentrated hydrochloric acid are added and the mixture is refluxed for 75 minutes. After concentrating under reduced pressure, the remaining oil is purified by column chromatography (silica gel/ethyl acetate) to remove by-products, then ethyl acetate:ethanol 10:1.5). 25 g of 1-methyl-3-[6-carbomethoxy-2-hexine-yl(1)]-4-hydroxymethyl-pyrrolidone [R$_F$ 0.14 (ethyl acetate)] are obtained.

n$_D$$^{20}$ = 1.5005 IR(CH$_2$Cl$_2$): = 3450 (OH), 1740 (C=O), 1690 (C=O) cm$^{-1}$ NMR:solvent: CDCl$_3$:N-CH$_3$: 2.82 ppm; O-CH$_3$: 3.64 ppm.

1-ISOPROPYL COMPOUND

This compound is prepared in analogous manner using as starting compound 1-isopropyl-4-(tetrahydropyranyl-hydroxymethyl)-pyrrolidone. $n_D^{20} = 1.4945$

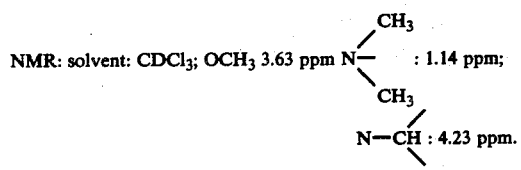

NMR: solvent: CDCl₃; OCH₃ 3.63 ppm

(b) ANODIC OXIDATION OF THE 1-ISOPROPYL COMPOUND

In an electrolytic cell having a capacity of about 60 ml 5.0 g of 1-isopropyl-3-[6-carbomethoxy-2-hexine-yl(1)]-4-hydroxymethylpyrrolidone-2 and 57.7 g of methanol are electrolyzed in the presence of 0.09 g of tetramethylammonium tetrafluoroborate as conducting salt. As electrodes two concentrically diposed platinum net cylinders having 225 meshes per cm² and diameters of 15 and 30 mm, respectively, and a height of 50 mm are immersed in the solution. The outer electrode is connected as anode. During electrolysis the temperature is maintained at about 10° C. After having switched on the electrolysis direct current, the anode current density is found to be 1 A/dm². After having passed 2.44 Faradays per mol of starting lactam the current is switched off. The calculated average cell tension is 31.2 volts.

After separation of the methanol by distillation under reduced pressure there are obtained by column chromatography (silica gel/ethyl acetate) 3.35 g of 1-isopropyl-3-[carbomethoxy-2-hexine-yl(1)]-4-hydroxymethyl-5-methoxypyrrolidone-2 ($R_F^1$ 0.61; $R_F^2$ 0.55 (ethyl acetate), corresponding to a material yield of 60.8% and to a current efficiency of 50.1% of the theory.

EXAMPLE 6

In an electrolytic cell as described in Example 1, but having a capacity of 400 ml 87.3 g of caprolactam and 247.1 g of methanol are electrolyzed in the presence of 1.24 g of tetramethylammonium tetrafluoroborate as conducting salt. The platinum net cylinders have a height of 100 mm. After having switched on the electrolysis direct current, the anode current density is found to be 3 A/dm². After having passed 3.0 Faradays per mole of ε-caprolactam, the current is switched off. The calculated average cell tension is 26.8 volts.

After working up by molecular distillation, 61.1 g of ε-methoxy-caprolactam (boiling point 106°-108° C. under 0.6 millibar; melting point 65°-66° C.) are obtained, corresponding to a material yield of 55.3% and a current efficiency of 36.9%.

EXAMPLE 7

In an electrolytic cell as described in Example 6 87.3 g of caprolactam and 247.1 g of methanol are electrolyzed in the presence of 9.7 g of potassium tetrafluoroborate as conducting salt. After having switched on the electrolysis direct current, the anode current density is 1 A/dm². The current is switched off after passage of 3.0 Faradays per mol of ε-caprolactam. The calculated average cell tension is 30.3 volts.

After working up by molecular distillation, 59.0 g of ε-methoxy-caprolactam (boiling point 106°-108° C. under 0.6 millibar; melting point 65°-66° C.) are obtained, corresponding to a material yield of 53.4% and a current efficiency of 35.6%.

EXAMPLE 8

In an electrolytic cell as described in Example 6 78.6 g of piperidone-2 and 253.9 g of methanol are electrolyzed in the presence of 1.28 g of tetramethylammonium tetrafluoroborate as conducting salt. After having switched on the electrolysis direct current, the anode current density is found to be 2 A/dm². After passage of 2.4 Faradays per mol of piperidone-2, the current is switched off. The calculated average cell tension is 12.4 volts.

After removal of the methanol and twofold recrystallization in di-isopropyl ether, 73.4 g of 6-methoxypiperidone-2 (melting point 110°-111° C.) are obtained, corresponding to a material yield of 71.1% and a current efficiency of 59.2%.

EXAMPLE 9

In an electrolytic cell as described in Example 6 87.3 g of ε-caprolactam and 247.1 g of methanol are electrolyzed in the presence of 8.4 g of sodium tetrafluoroborate as conducting salt. After having switched on the electrolysis direct current, the anode current density is found to be 3 A/dm². After passage of 3.0 Faradays per mol of ε-caprolactam the current is disconnected. The average cell tension is calculated to be 12.9 volts. After working up by molecular distillation, 80.0 g of ε-methoxy-ε-caprolactam are obtained, corresponding to a material yield of 72.4% and a current efficiency of 48.3%.

EXAMPLE 10

A test is carried out under the conditions of Example 9 with the exception, however, that a mixture of 4.2 g of sodium tetrafluoroborate and 5.9 g of tetramethylammonium tetrafluoroborate is used as conducting salt. After disconnection of the current, the average cell tension is calculated to be 18.7 volts. By working up by molecular distillation 78.4 g of ε-methoxy-ε-caprolactam are obtained, corresponding to a material yield of 71,0% and to a current efficiency of 47.3%.

EXAMPLE 11

In an electrolytic cell as described in Example 6 72.24 g of laurinolactam and 293.33 g of methanol are electrolyzed in the presence of 0.6 g of tetramethylammonium tetrafluoroborate as conducting salt. After having switched on the electrolysis direct current, the anode current density is found to be 2 A/dm². After having passed 3.5 Faradays per mol of laurinolactam, the current is disconnected. The calculated average cell tension is 48.1 volts.

After working up and recrystallization 42.4 g of ω-methoxylaurinolactam of the formula

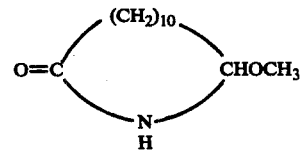

(melting point 153.5°-154.5° C.) are obtained, corresponding to a material yield of 50.9% and a current efficiency of 29.1%.

EXAMPLE 12

In an electrolytic cell as described in Example 1 16.7 g of caprolactam and 75.8 g of methanol are electrolyzed in the presence of 0.19 g of tetramethylammonium tetrafluoroborate as conducting salt. After having switched on the electrolysis direct current, the anode current density is 1 A/dm². The current is disconnected after having passed 3.0 Faradays per mol of caprylolactam. The calculated average cell tension is 35.2 volts.

After working up by molecular distillation 11.6 g of ω-methoxycaprylolactam of the formula

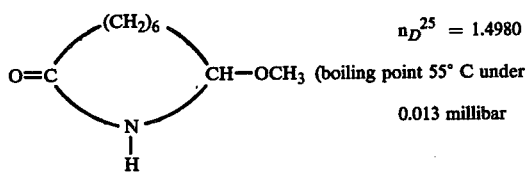

$n_D^{25} = 1.4980$ (boiling point 55° C under 0.013 millibar are obtained, corresponding to a material yield of 57.2% and a current efficiency of 38.3%.

What is claimed is:

1. A compound of the formula

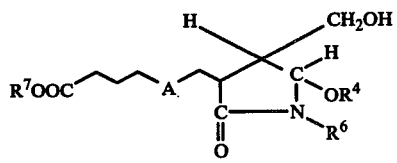

in which

A represents —CH≡C—, —CH=CH— or —CH—CH—

R⁴ represents an alkyl group having from 1 to 4 carbon atoms,

R⁶ represents hydrogen or a branched alkyl group having from 3 to 10 carbon atoms with a secondary or tertiary N-α-C atom, and R⁷ represents an alkyl group having from 1 to 4 carbon atoms, a cycloalkyl group having 5 or 6 carbon atoms or an carbocyclic aralkyl group of 6 to 9 carbon atoms.

2. A compound as claimed in claim 1 in which A stands for —C≡C—, R⁴ and R⁷ stand for CH₃ and R⁶ stands for

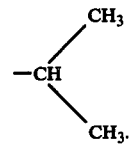

3. 1-methyl-3-[6-carbomethoxy-2-hexine-yl(1)]-4-hydroxymethyl-5-methoxy-pyrrolidone.

4. 1-isopropyl-3-[6-carbomethoxy-2-hexine-yl(1)]-4-hydroxymethyl-5-methoxy-pyrrolidone.

* * * * *